(12) United States Patent
Cronin

(10) Patent No.: US 12,170,145 B2
(45) Date of Patent: Dec. 17, 2024

(54) SYSTEM AND METHOD FOR SOFTWARE AND HARDWARE ACTIVATION BASED ON REAL-TIME HEALTH PARAMETERS

(71) Applicant: Know Labs, Inc., Seattle, WA (US)

(72) Inventor: John Cronin, Williston, VT (US)

(73) Assignee: KNOW LABS, INC., Seattle, WA (US)

( * ) Notice: Subject to any disclaimer, the term of this patent is extended or adjusted under 35 U.S.C. 154(b) by 0 days.

(21) Appl. No.: 18/188,007

(22) Filed: Mar. 22, 2023

(65) Prior Publication Data
US 2024/0321442 A1   Sep. 26, 2024

(51) Int. Cl.
| | |
|---|---|
| G16H 40/63 | (2018.01) |
| A61B 5/00 | (2006.01) |
| A61B 5/145 | (2006.01) |
| G16H 15/00 | (2018.01) |

(52) U.S. Cl.
CPC ........... *G16H 40/63* (2018.01); *A61B 5/0026* (2013.01); *A61B 5/14532* (2013.01); *G16H 15/00* (2018.01)

(58) Field of Classification Search
CPC ...... G16H 40/63; G16H 15/00; A61B 5/0026; A61B 5/14532
See application file for complete search history.

(56) References Cited

U.S. PATENT DOCUMENTS

| | | |
|---|---|---|
| 4,202,000 A | 5/1980 | Carballes |
| 8,223,021 B2 | 7/2012 | Goodnow et al. |
| 8,882,670 B2 | 11/2014 | Hancock |
| 9,198,607 B2 | 12/2015 | Fischer |

(Continued)

FOREIGN PATENT DOCUMENTS

| | | |
|---|---|---|
| EP | 3146898 B1 | 11/2018 |
| EP | 3981329 A1 | 4/2022 |

(Continued)

OTHER PUBLICATIONS

Juan et al., Glucose Concentration Measurement in Human Blood Plasma Solutions with Microwave Sensors, Aug. 31, 2019, Sensors, pp. 1-15. (Year: 2019).*

(Continued)

*Primary Examiner* — Christopher L Gilligan
(74) *Attorney, Agent, or Firm* — HSML P.C.

(57) ABSTRACT

A system which includes an apparatus for generating radio frequency scanning data which includes a transmitter for transmitting radio waves below the skin surface of a person and a two-dimensional array of receive antennas for receiving the radio waves, including a reflected portion of the transmitted radio waves that is reflected from a blood vessel of the person. The wave signal is compared to known standard waveforms, and similar waveforms are input into a machine learning algorithm to determine one or more health parameters of the person. The system then notifies the person and/or health professionals of the person's health status. The health parameters can be used to trigger other software and hardware modules such as another measurement device, a medication scheduler or alert, medical recommendations, guidance software, a virtual assistant, or any other hardware and/or software which may help the patient or health professionals.

9 Claims, 6 Drawing Sheets

(56) References Cited

U.S. PATENT DOCUMENTS

| | | |
|---|---|---|
| 9,864,024 B2 | 1/2018 | Vester |
| 10,149,629 B2 | 12/2018 | Szczepaniak et al. |
| 10,478,101 B1 | 11/2019 | Cespedes et al. |
| 10,548,503 B2 | 2/2020 | Bosua |
| 10,617,296 B2 | 4/2020 | Sloan et al. |
| 10,856,766 B2 | 12/2020 | Leabman |
| 10,912,500 B2 | 2/2021 | Poeze et al. |
| 10,956,950 B2 | 3/2021 | Al-Ali et al. |
| 11,031,970 B1 | 6/2021 | Bosua |
| 11,033,208 B1 | 6/2021 | Bosua |
| 11,058,317 B1 | 7/2021 | Bosua |
| 11,058,331 B1 | 7/2021 | Bosua |
| 11,063,373 B1 | 7/2021 | Bosua |
| 11,193,923 B2 | 12/2021 | Bosua |
| 11,202,582 B2 | 12/2021 | Verkruijsse et al. |
| 11,223,383 B2 | 1/2022 | Bosua |
| 11,234,618 B1 | 2/2022 | Bosua et al. |
| 11,234,619 B2 | 2/2022 | Bosua |
| 11,244,753 B2 | 2/2022 | Haggerty et al. |
| 11,284,819 B1 | 3/2022 | Bosua et al. |
| 11,284,820 B1 | 3/2022 | Bosua et al. |
| 11,291,374 B2 | 4/2022 | Lee et al. |
| 11,298,037 B2 | 4/2022 | Leabman |
| 11,350,830 B2 | 6/2022 | McKenna et al. |
| 11,360,188 B2 | 6/2022 | Leabman |
| 11,367,525 B2 | 6/2022 | Addison et al. |
| 11,389,091 B2 | 7/2022 | Bosua |
| 11,389,093 B2 | 7/2022 | Triman et al. |
| 11,426,104 B2 | 8/2022 | Schurman et al. |
| 11,596,330 B2 * | 3/2023 | Hayter ............... A61B 5/14532 |
| 2003/0036713 A1 | 2/2003 | Bouton et al. |
| 2003/0235817 A1 | 12/2003 | Bartkowiak et al. |
| 2004/0065158 A1 | 4/2004 | Schrepfer et al. |
| 2004/0127777 A1 | 7/2004 | Ruchti et al. |
| 2004/0133086 A1 | 7/2004 | Ciurczak et al. |
| 2006/0001551 A1 | 1/2006 | Kraft et al. |
| 2008/0083617 A1 | 4/2008 | Simpson et al. |
| 2008/0214918 A1 | 9/2008 | Brister et al. |
| 2009/0099436 A1 | 4/2009 | Brister et al. |
| 2009/0137887 A1 | 5/2009 | Shariati et al. |
| 2009/0275814 A1 | 11/2009 | Watanabe et al. |
| 2009/0322513 A1 | 12/2009 | Hwang et al. |
| 2010/0041969 A1 | 2/2010 | Beise |
| 2011/0028814 A1 | 2/2011 | Petersen et al. |
| 2011/0087117 A1 | 4/2011 | Tremper et al. |
| 2013/0096396 A1 | 4/2013 | Riedel |
| 2013/0184599 A1 | 7/2013 | Friedman et al. |
| 2014/0213870 A1 | 7/2014 | Hsu et al. |
| 2015/0257698 A1 | 9/2015 | Spratt et al. |
| 2016/0051171 A1 | 2/2016 | Pikov et al. |
| 2016/0157733 A1 | 6/2016 | Gil |
| 2016/0309535 A1 | 10/2016 | Myoung et al. |
| 2016/0361002 A1 | 12/2016 | Palikaras et al. |
| 2017/0095667 A1 | 4/2017 | Yakovlev et al. |
| 2017/0215811 A1 * | 8/2017 | Newberry ............ A61B 5/14551 |
| 2018/0028824 A1 | 2/2018 | Pivonka et al. |
| 2018/0035901 A1 | 2/2018 | Cronin et al. |
| 2018/0042559 A1 * | 2/2018 | Cabrera, Jr. ............ G06F 3/0484 |
| 2018/0132766 A1 | 5/2018 | Lee et al. |
| 2018/0242920 A1 | 8/2018 | Hresko et al. |
| 2019/0008422 A1 | 1/2019 | Leath et al. |
| 2019/0053741 A1 | 2/2019 | Chaudhry |
| 2019/0104939 A1 | 4/2019 | Costantine et al. |
| 2019/0142313 A1 * | 5/2019 | Abou Ismail ........ A61B 5/0022 |
| | | 600/316 |
| 2019/0252079 A1 | 8/2019 | Constantin et al. |
| 2019/0269853 A1 | 9/2019 | Doyle et al. |
| 2019/0374135 A1 | 12/2019 | Poeze et al. |
| 2019/0388000 A1 | 12/2019 | Costantine et al. |
| 2020/0054255 A1 | 2/2020 | Conrad et al. |
| 2020/0057163 A1 | 2/2020 | Bromberg |
| 2020/0113485 A1 | 4/2020 | Wybo et al. |
| 2020/0146584 A1 | 5/2020 | Bosua |
| 2020/0187791 A1 | 6/2020 | Leabman |
| 2020/0187792 A1 | 6/2020 | Leabman |
| 2020/0187793 A1 | 6/2020 | Leabman |
| 2020/0187812 A1 | 6/2020 | Leabman |
| 2020/0187813 A1 | 6/2020 | Leabman |
| 2020/0187814 A1 | 6/2020 | Leabman |
| 2020/0187815 A1 | 6/2020 | Leabman |
| 2020/0187816 A1 | 6/2020 | Leabman |
| 2020/0187817 A1 | 6/2020 | Leabman |
| 2020/0187818 A1 | 6/2020 | Leabman |
| 2020/0187819 A1 | 6/2020 | Leabman |
| 2020/0187820 A1 | 6/2020 | Leabman |
| 2020/0187836 A1 | 6/2020 | Leabman |
| 2020/0187837 A1 | 6/2020 | Leabman |
| 2020/0187867 A1 | 6/2020 | Leabman |
| 2020/0191909 A1 | 6/2020 | Leabman |
| 2020/0191932 A1 | 6/2020 | Leabman |
| 2020/0191933 A1 | 6/2020 | Leabman |
| 2020/0191944 A1 | 6/2020 | Leabman |
| 2020/0191945 A1 | 6/2020 | Leabman |
| 2020/0191947 A1 | 6/2020 | Leabman |
| 2020/0192426 A1 | 6/2020 | Leabman |
| 2020/0192427 A1 | 6/2020 | Leabman |
| 2020/0192428 A1 | 6/2020 | Leabman |
| 2020/0193326 A1 | 6/2020 | Leabman |
| 2020/0195197 A1 | 6/2020 | Leabman |
| 2020/0195293 A1 | 6/2020 | Leabman |
| 2021/0134431 A1 | 5/2021 | Garcia et al. |
| 2021/0137468 A1 | 5/2021 | Katragadda et al. |
| 2021/0186357 A1 | 6/2021 | Bosua et al. |
| 2021/0194531 A1 | 6/2021 | Bosua |
| 2021/0205180 A1 * | 7/2021 | Pugsley ................ G16H 20/13 |
| 2021/0219925 A1 | 7/2021 | Au et al. |
| 2021/0259571 A1 | 8/2021 | Bosua |
| 2021/0259592 A1 | 8/2021 | Bosua |
| 2021/0259593 A1 | 8/2021 | Bosua |
| 2021/0350896 A1 | 11/2021 | Shelton, IV et al. |
| 2022/0015695 A1 | 1/2022 | Margarito et al. |
| 2022/0031254 A1 | 2/2022 | Al-Ali et al. |
| 2022/0071527 A1 | 3/2022 | Bosua |
| 2022/0074870 A1 | 3/2022 | Bosua |
| 2022/0077918 A1 | 3/2022 | Bosua et al. |
| 2022/0108788 A1 | 4/2022 | Shelton, IV et al. |
| 2022/0108805 A1 | 4/2022 | Lee |
| 2022/0151553 A1 | 5/2022 | Bosua |
| 2022/0192494 A1 | 6/2022 | Leabman |
| 2022/0192522 A1 | 6/2022 | Leabman |
| 2022/0192531 A1 | 6/2022 | Leabman |
| 2022/0233119 A1 | 7/2022 | Shelton, IV et al. |
| 2022/0233241 A1 | 7/2022 | Shelton, IV et al. |
| 2022/0233254 A1 | 7/2022 | Shelton, IV et al. |
| 2022/0238216 A1 | 7/2022 | Shelton, IV et al. |
| 2022/0248965 A1 | 8/2022 | O'Brien et al. |
| 2022/0248984 A1 | 8/2022 | Poeze et al. |
| 2022/0257199 A1 | 8/2022 | Breton et al. |
| 2022/0287649 A1 | 9/2022 | Leabman |
| 2022/0296111 A1 * | 9/2022 | Leabman ............... A61B 5/681 |
| 2022/0322976 A1 | 10/2022 | Edla et al. |
| 2023/0263439 A1 | 8/2023 | Cheng et al. |
| 2023/0390466 A1 * | 12/2023 | Johnson ................ G16H 10/40 |
| 2024/0062870 A1 | 2/2024 | Rosenberg et al. |
| 2024/0225490 A1 * | 7/2024 | Windmiller .......... A61B 5/0004 |

FOREIGN PATENT DOCUMENTS

| | | |
|---|---|---|
| JP | 2012125382 | 7/2012 |
| JP | 2014147637 | 8/2014 |
| KR | 10-1247513 | 3/2013 |
| KR | 10-2013-0142016 | 12/2013 |
| KR | 1020160081740 | 7/2016 |
| KR | 10-2022-0052078 | 4/2022 |
| WO | 2008/154759 | 12/2008 |
| WO | 2009/082286 | 7/2009 |
| WO | 2010/045460 | 4/2010 |
| WO | 2016/127130 | 8/2016 |
| WO | 2017163245 | 9/2017 |
| WO | 2018/111690 | 6/2018 |
| WO | 2019071138 | 4/2019 |
| WO | 2019/178524 | 9/2019 |
| WO | 2019182638 | 9/2019 |
| WO | 2019217461 | 11/2019 |

(56) References Cited

FOREIGN PATENT DOCUMENTS

| | | | |
|---|---|---|---|
| WO | 2020006077 | 1/2020 | |
| WO | 2020037171 | 2/2020 | |
| WO | 2021198045 A1 | 10/2021 | |
| WO | WO-2021245459 A1 * | 12/2021 | ......... G01N 33/6893 |
| WO | 2022026623 A1 | 2/2022 | |
| WO | 2022/157706 | 7/2022 | |
| WO | 2022/184623 | 9/2022 | |
| WO | 2022/235714 | 11/2022 | |
| WO | 2023/028367 | 3/2023 | |

OTHER PUBLICATIONS

Hanna, J. et al., "Noninvasive, wearable, and tunable electromagnetic multisensing system for continuous glucose monitoring, mimicking vasculature anatomy," Science Advances, 6, eaba5320, 2020 (11 pages).

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

Qiang et al., "Quantitative detection of glucose level based on radiofrequency patch biosensor combined with volume-fixed structures," Biosensors and Bioelectronics 98:357-363, 2017.

Shaker, G. et al., "Non-Invasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

Stojanovic, R. et al., "An optical sensing approach based on light emitting diodes," Journal of Physics: Conference Series 76 (2007), pp. 1-6.

Rossiter, J. et al., "A novel tactile sensor using a matrix of LEDs operating in both photoemitter and photodetector modes," Proc of 4th IEEE International Conference on Sensors (IEEE Sensors 2005), pp. 994-997.

Majewski et al., "Erroneous Causes of Point-of-Care Glucose Readings", Cureus, Mar. 19, 2023, www.ncbi.nlm.nih.gov/pmc/articles/PMC10112488, 4 pages.

C, Alex, "Heart Rate is Here", Making Sense of Heart Rate Data With Veri, Mar. 14, 2023, www.veri.co/learn/heart-rate-data-veri, 11 pages.

Dunbar, Brian, "What are Radio Waves?" NASA, Aug. 31, 2018, www.nasa.gov/directorates/heo/scan/commnications/outreach/funfacts/what_are_raido_waves, 2 pages.

International Search Report and Written Opinion for Application No. PCT/US2024/020760 mailed Jul. 2, 2024.

Nøstbakken, "Cancellation of Movement Artifacts in Glucosesensor Data," NTNU Open, NTNU, Jun. 5, 2017, ntnuopen.ntnu.no/ntnu-xmlui/handle/11250/2457154. Accessed Jan. 13, 2024. (Year: 2017).

Surgery Definition & Meaning, Aug. 22, 2023, Merriam Webster Dictionary (Year: 2023).

* cited by examiner

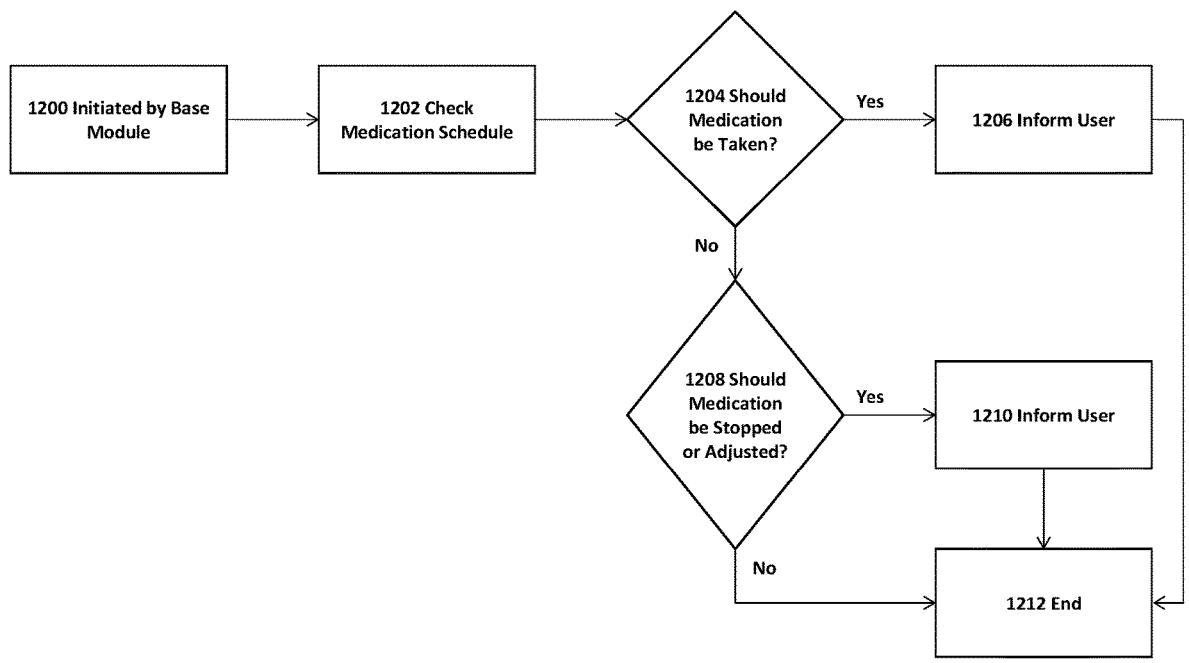

FIG.12

| Parameter | Range | Module | Action |
|---|---|---|---|
| Glucose | 120-180 mg/dL | Notification Module | Notify Patient - Elevated Glucose |
| Glucose | 120-180 mg/dL | Assistant Module | Elevated Glucose Questionnaire |
| Glucose | >180 mg/dL | Medication Module | Insulin Reminder/Warning |
| Cortisol | >690 nmol/L | Notification Module | Notify Patient - High Stress |
| Cortisol | >690 nmol/L | Report Schedule Module | Schedule Weekly Report and Record Elevated Incident |
| Cortisol | >690 nmol/L | Guidance Module | Guide Patient in Meditative Exercises |
| Cortisol | >800 nmol/L | Guidance Module | Suggest Doctor Test for Cushing's Syndrome |
| - | - | - | - |
| - | - | - | - |

FIG.13

SYSTEM AND METHOD FOR SOFTWARE AND HARDWARE ACTIVATION BASED ON REAL-TIME HEALTH PARAMETERS

FIELD

The present disclosure is generally related to systems and methods of monitoring health parameters and, more particularly, relates to a system and a method of monitoring a signal that corresponds to an analyte, such as the blood glucose level, in a user.

BACKGROUND

The current method of blood analysis can be invasive, time-consuming, and may not provide real-time results, leading to medical guidance that is less accurate and less effective.

Currently, medical professionals may not have access to real-time and noninvasive analyte data, which limits their ability to make informed decisions about patient care.

Using traditional, invasive blood analysis methods during surgery can be risky and result in delays. The use of real-time noninvasive analyte data in surgery is necessary to enhance surgical outcomes and improve patient care.

DESCRIPTION OF THE DRAWINGS

FIG. 12: Illustrates an example operation of a Medication Module, according to an embodiment.

FIG. 13: Illustrates a Parameter Range Database, according to an embodiment.

DETAILED DESCRIPTION

Figure 1:
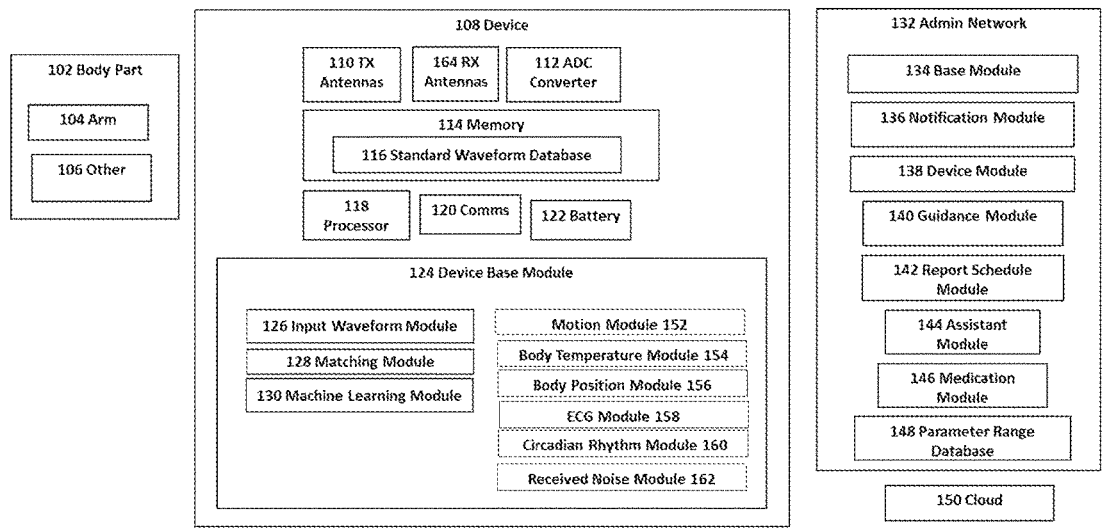
FIG. 1: Illustrates a system for radio frequency health monitoring, according to an embodiment.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

U.S. Pat. Nos. 10,548,503, 11,063,373, 11,058,331, 11,033,208, 11,284,819, 11,284,820, 10,548,503, 11,234,619, 11,031,970, 11,223,383, 11,058,317, 11,193,923, 11,234,618, 11,389,091, U.S. 2021/0259571, U.S. 2022/0077918, U.S. 2022/0071527, U.S. 2022/0074870, U.S. 2022/0151553, are each individually incorporated herein by reference in its entirety.

A system for radio frequency health monitoring is described. This system comprises a body part 102, which the device 108 is attached or in proximity to. The body part 102 may be an arm 104. The body part 102 may be the other arm of the patient or another body part 106 besides an arm, such as a leg, finger, chest, head, or any other body part from which useful medical parameters can be taken. The system may further comprise the device 108, which may be a wearable and portable device such as, but not limited to, a cell phone, a smartwatch, a tracker, a wearable monitor, a wristband, and a personal blood monitoring device. The system may further comprise a set of TX antennas 110 and RX antennas 164. TX antennas 110 may be configured to transmit RF signals in the RF Activated Range from 500 MHZ to 300 GHZ. In one embodiment, a pre-defined frequency may correspond to a range suitable for the human body. For example, the one or more TX antennas 110 transmit radio frequency signals at a range of 120-126 GHz. Successively, the one or more RX antennas 164 may be configured to receive the RF signals in response to the TX RF signal. The system may further comprise an ADC converter 112, which may be configured to convert the RF signals from an analog signal into a digital processor readable format. The system may further comprise memory 114, which may be configured to store the transmitted RF signals by the one or more TX antennas 110 and receive a portion of the received RF signals from the one or more RX antennas 164. Further, the memory 114 may also store the converted digital processor readable format by the ADC converter 112. The memory 114 may include suitable logic, circuitry, and/or interfaces that may be configured to store a machine code and/or a computer program with at least one code section executable by the processor 118. Examples of implementation of the memory 114 may include, but are not limited to, Random Access Memory (RAM), Read Only Memory (ROM), Hard Disk Drive (HDD), and/or a Secure Digital (SD) card.

The system may further comprise a standard waveform database 116, which may contain standard waveforms for known patterns. These may be raw or converted device readings from patients or persons with known conditions. For example, the standard waveform database 116 may include raw or converted device readings from the patient, for example the right arm, known to have diabetes or an average of multiple patients. This data can be compared to readings from a person with an unknown condition to determine if the waveforms from that person match any of the known standard waveforms.

The system may further comprise a processor 118, which may facilitate the operation of the device 108 according to the instructions stored in the memory 114. The processor 118 may include suitable logic, circuitry, interfaces, and/or code that may be configured to execute a set of instructions stored in the memory 114.

The system may further comprise comms 120, which may communicate with a network. Examples of networks may include, but are not limited to, the Internet, a cloud network, a Wireless Fidelity (Wi-Fi) network, a Wireless Local Area Network (WLAN), a Local Area Network (LAN), Long Term Evolution (LTE), and/or a Metropolitan Area Network (MAN).

The system may further comprise a battery 122, which may power hardware modules of the device 108. The device 108 may be configured with a charging port to recharge the battery 122. Charging of the battery 122 may be achieved via wired or wireless means.

The system may further comprise a device base module 124, which may be configured to store instructions for executing the computer program on the converted digital processor readable format of the ADC converter 112. The device base module 124 may be configured to facilitate the operation of the processor 118, the memory 114, the TX antennas 110 and RX antennas 164, and the comms 120. Further, the device base module 124 may be configured to create polling of the RF Activated Range signals from 500 MHZ to 300 GHZ. It can be noted that the device base module 124 may be configured to filter the RF Activated Range signals from 500 MHZ to 300 GHZ received from the one or more RX antennas 164.

The system may further comprise an input waveform module 126, which may extract a radio frequency waveform from memory. This may be the raw or converted data recording from the RX antennas 164 from a patient wearing the device 108. If the entire radio frequency is too long for effective matching, the input waveform module 126 may select a time interval within the data set. This input waveform may then be sent to the matching module 128.

The system may further comprise a matching module 128, which may match the input waveform and each of the standard waveforms in the standard waveform database 116 by performing a convolution and/or cross-correlation of the input waveform and the standard waveform. These convolutions and/or cross-correlations are then sent to the machine learning module.

The system may further comprise a machine learning module 130 which has been trained to identify health parameters based on the convolution and/or cross-correlations of the input and standard waveforms. The machine learning module 130 receives the convolutions and cross-correlations from the matching module 128 and outputs any health parameters identified.

In some embodiments, the device base module 124 may utilize a motion module 152 that includes at least one sensor from the group of an accelerometer, a gyroscope, an inertial movement sensor, or other similar sensor. The motion module 152 may have its own processor or utilize the processor 118 to calculate the user's movement. Motion from the user will change the blood volume in a given portion of their body and the blood flow rate in their circulatory system. This may cause noise, artifacts, or other errors in the real-time signals received by the RX antennas 164. The motion module 152 may compare the calculated motion to a motion threshold stored in memory 114. For example, the motion threshold could be movement of more than two centimeters in one second. The motion threshold could be near zero to ensure the user is stationary when measuring to ensure the least noise in the RF signal data. When calculated motion levels exceed the motion threshold, the motion module 152 may flag the RF signals collected at the time stamp corresponding to the motion as potentially inaccurate. In some embodiments, the motion module 152 may compare RF signal data to motion data over time to improve the accuracy of the motion threshold. The motion module 152 may alert the user, such as with an audible beep or warning or a text message or alert to a connected mobile device. The alert would signal the user that they are moving too much to get an accurate measurement. The motion module 152 may update the standard waveform database 116 with the calculated motion of the user that corresponds with the received RF signal data. In this manner, the motion module 152 may be simplified to just collect motion data and allow the device base module 124 to determine if the amount of motion calculated exceeds a threshold that would indicate the received RF signal data is too noisy to be relied upon for a blood glucose measurement.

The device base module 124 may utilize a body temperature module 154 that includes at least one sensor from the group of a thermometer, a platinum resistance thermometer (PRT), a thermistor, a thermocouple, or another temperature sensor. The body temperature module 154 may have its own processor or utilize the processor 118 to calculate the temperature of the user or the user's environment. The user's body temperature, the environmental temperature, and the difference between the two will change the blood volume in a given part of their body and the blood flow rate in their circulatory system. Variations in temperature from the normal body temperature or room temperature may cause noise, artifacts, or other errors in the real-time signals received by the RX antennas 164. The body temperature module 154 may compare the measured temperature to a threshold temperature stored in memory 114. For example, the environmental temperature threshold may be set at zero degrees Celsius because low temperatures can cause a temporary narrowing of blood vessels which may increase the user's blood pressure. When the measured temperature exceeds the threshold, the body temperature module 154 may flag the RF signals collected at the time stamp corresponding to the temperature as potentially being inaccurate. In some embodiments, the body temperature module 154 may compare RF signal data to temperature data over time to improve the accuracy of the temperature threshold. The body temperature module 154 may alert the user, such as with an audible beep or warning or a text message or alert to a connected mobile device. The alert would signal to the user that their body temperature, or the environmental temperature is not conducive to getting an accurate measurement. The body temperature module 154 update the standard waveform database 116 with the measured user or environmental temperature that corresponds with the received RF signal data. In this manner, the body temperature module 154 may be simplified to just collect temperature data and allow the device base module 124 to determine if the temperature measure exceeds a threshold that would indicate the received RF signal data is too noisy to be relied upon for a blood glucose measurement.

The device base module 124 may utilize a body position module 156 that includes at least one sensor from the group of an accelerometer, a gyroscope, an inertial movement sensor, or another similar sensor. The body position module 156 may have its own processor or utilize the processor 118 to estimate the user's position. The user's body position may change the blood volume in a given part of their body and the blood flow rate in their circulatory system. This may cause noise, artifacts, or other errors in the real-time signals received by the RX antennas 164. The body position module 156 may compare the estimated position to a body position threshold stored in memory 114. For example, the monitoring device 102 may be on the user's wrist, and the body position threshold may be based on the relative position of the user's hand to their heart. When a user's hand is lower than their heart, their blood pressure will increase, with this effect being more pronounced the longer the position is maintained. Conversely, the higher a user holds their arm above their heart, the lower the blood pressure in their hand. The body position threshold may include some minimum amount of time the estimated body position occurs. When the estimated position exceeds the threshold, the body position module 156 may flag the RF signals collected at the time stamp corresponding to the body position as potentially being inaccurate. In some embodiments, the body position module 156 may compare RF signal data to motion data over time to improve the accuracy of the body position threshold. The body position data may also be used to estimate variations in parameters such as blood pressure that corresponds to the body position data to improve the accuracy of the measurements taken when the user is in that position. The body position module 156 may alert the user, such as with an audible beep or warning or a text message or alert to a connected mobile device. The alert would signal to the user that their body position is not conducive to getting an accurate measurement. The body position module 156 may update the standard waveform database 116 with the estimated body position data that corresponds with the received RF signal data. In this manner, the body position module 156 may be simplified to just collect temperature data and allow the device base module 124 to determine if the body position exceeded a threshold that would indicate the received RF signal data is too noisy to be relied upon for a blood glucose measurement.

The device base module 124 may utilize an ECG module 158 that includes at least one electrocardiogram sensor. The ECG module 158 may have its own processor or utilize the processor 118 to record the electrical signals that correspond with the user's heartbeat. The user's heartbeat will impact blood flow. Measuring the ECG data may allow the received RF data to be associated with peak and minimum cardiac output so as to create a pulse waveform allowing for the estimation of blood volume at a given point in the wave of ECG data. Variations in blood volume may cause noise, artifacts, or other errors in the real-time signals received by the RX antennas 164. The ECG module 158 may compare the measured cardiac data to a threshold stored in memory 114. For example, the threshold may be a pulse above 160 bpm, as the increased blood flow volume may cause too much noise in the received RF signal data to accurately measure the blood glucose. When the ECG data exceeds the threshold, the ECG module 158 may flag the RF signals collected at the time stamp corresponding to the ECG data as potentially being inaccurate. In some embodiments, the ECG module 158 may compare RF signal data to ECG data over time to improve the accuracy of the ECG data threshold or to improve the measurement of glucose at a given point in the cycle between peak and minimum cardiac output. The ECG module 158 may alert the user, such as with an audible beep or warning or a text message or alert to a connected mobile device. The alert would signal to the user that their heart rate is not conducive to getting an accurate measurement or requires additional medical intervention. The ECG module 158 may update the standard waveform database 116 with the measured ECG data that corresponds with the received RF signal data. In this manner, the ECG module 158 may be simplified to just collect ECG data and allow the device base module 124 to determine if the ECG data exceeded a threshold that would indicate the received RF signal data is too noisy to be relied upon for a blood glucose measurement.

The device base module 124 may utilize a circadian rhythm module 160 that includes at least one sensor measuring actigraphy, wrist temperature, light exposure, and heart rate. The circadian rhythm module 160 may have its own processor or utilize the processor 118 to calculate the user's circadian health. Blood pressure follows a circadian rhythm in that it increases upon waking in the morning and decreases during sleeping at night. People with poor circadian health will often have higher blood pressure. These variations in blood pressure can cause noise, artifacts, or other errors or inaccuracies in the real-time signals received by the RX antennas 164. The circadian rhythm module 160 may compare the circadian data to a threshold stored in memory 114. For example, the threshold may be less than 6 hours of sleep in the last 24 hours. When the observed circadian health data exceeds the threshold, the circadian rhythm module 160 may flag the RF signals collected at the time stamp corresponding to circadian health as potentially being inaccurate or needing an adjustment to account for the expected increase in the user's blood pressure. In some embodiments, the circadian rhythm module 160 may compare RF signal data to sleep data over time to improve the accuracy of the circadian rhythm thresholds. The circadian rhythm module 160 may alert the user, such as with an audible beep or warning, or a text message or alert to a connected mobile device. The alert would signal to the user that their recent sleep patterns are not conducive to getting an accurate measurement. The circadian rhythm module 160 may update the standard waveform database 116 with the measured circadian data that corresponds with the received RF signal data. In this manner, the circadian rhythm module 160 may be simplified to just collect circadian rhythm data and allow the device base module 124 to determine if the measure exceeded a threshold that would indicate the received RF signal data is too noisy to be relied upon for a blood glucose measurement, or if an alternative transfer function should be used to compensate for the detected circadian health.

The device base module 124 may include a received noise module 162 that includes at least one sensor measuring background signals such as RF signals, Wi-Fi, and other electromagnetic signals that could interfere with the signals received by the RX antennas 164. The received noise module 162 may have its own processor or utilize the processor 118 to calculate the level of background noise being received. Background noise may interfere with or cause noise, artifacts, or other errors or inaccuracies in the real-time signals received by the RX antennas 164. The received noise module 162 may compare the level and type of background noise to a threshold stored in memory 114. The threshold may be in terms of field strength (volts per meter and ampere per meter) or power density (watts per square meter). For example, the threshold may be RF radiation greater than 300 µW/m2. When the background noise data exceeds the threshold, the received noise module 162 may flag the RF signals collected at the time stamp corresponding to background noise levels as potentially being inaccurate. In some embodiments, the received noise module 162 may compare RF signal data to background noise over time to improve the accuracy of the noise thresholds. The received radiation module may alert the user, such as with an audible beep or warning, a text message, or an alert to a connected mobile device. The alert would signal to the user that the current level of background noise is not conducive to getting an accurate measurement.

The received noise module 162 may update the standard waveform database 116 with the background noise data that corresponds with the received RF signal data. In this manner, the received noise module 162 may be simplified to just collect background noise data and allow the device base module 124 to determine if the measure exceeded a threshold that would indicate the received RF signal data is too noisy to be relied upon for a blood glucose measurement, or if an alternative transfer function should be used to compensate for the noise.

In embodiments, one or more of memory 114, standard waveform database 116, input waveform module 126, matching module 128, the machine learning module 130, the motion module 152, the body temperature module 154, the body position module 156, the ECG module 158, the circadian rhythm module 160, and/or the received noise module 162 can be provided on one or more separate devices, such as cloud server, a networked device, or the like. In such embodiments, the comms 120 can be used to communicate with the cloud server or the networked device to access the memory 114, standard waveform database 116, input waveform module 126, matching module 128, the machine learning module 130, the motion module 152, the body temperature module 154, the body position module 156, the ECG module 158, the circadian rhythm module 160, and/or the received noise module 162 by way of any suitable network.

The system may further comprise an admin network 132, which may be a computer or network of computers which receive information from the device 108 and execute one or more software modules. The admin network 132 may connect to the device 108 directly or may receive and send data over the cloud 150 or communication network.

The system may further comprise a base module 134, which may receive parameters sent to the admin network 132 from the device 108 and compare those parameters to ranges in the parameter range database 148. If the received parameter falls into a range that requires an action by the system, such as notifying a doctor or activating a device, then the base module 134 may initiate the modules that perform that action.

The system may further comprise a notification module 136, which may determine if any of the health parameters require a notification. If so, the patient and/or the patient's medical care providers may be notified.

The system may further comprise a device module 138, which may activate other devices based on the received health parameters. These devices may be the same as the device 108 or may be other devices such as a blood pressure monitor, blood oxygen monitor, infusion pump, ventilator, etc.

The system may further comprise a guidance module 140, which may guide or advise doctors and/or other medical staff when further analysis or actions are required. The guidance module 140 may also guide the patient in actions they may be able to take to improve their health parameters.

The system may further comprise a report schedule module 142, which may send scheduled detailed reports on a patient's health parameters to the patient's doctor or other health professionals.

The system may further comprise an assistant module 144, which may activate a virtual assistant to collect information from the patient and/or give medical advice to the patient based on their health parameters.

The system may further comprise a medication module 146, which may inform the patient and/or medical professionals when medication is needed based on the patient's health parameters and/or a medication schedule.

The system may further comprise a parameter range database 148, which may contain ranges of health parameter values and an action or actions which are associated with that range. When health parameters are within range, the associated actions may be carried out by the modules of the system.

The system may further comprise a Cloud 150 or communication network, which may be a wired and/or wireless network. The communication network, if wireless, may be implemented using communication techniques such as Visible Light Communication (VLC), Worldwide Interoperability for Microwave Access (WiMAX), Long Term Evolution (LTE), Wireless Local Area Network (WLAN), Infrared (IR) communication, Radio waves, and other communication techniques known in the art. The communication network may allow ubiquitous access to shared pools of configurable system resources and higher-level services that can be rapidly provisioned with minimal management effort, often over the Internet, and relies on sharing of resources to achieve coherence and economies of scale, like a public utility, while third-party clouds enable organizations to focus on their core businesses instead of expending resources on computer infrastructure and maintenance.

Figure 2:
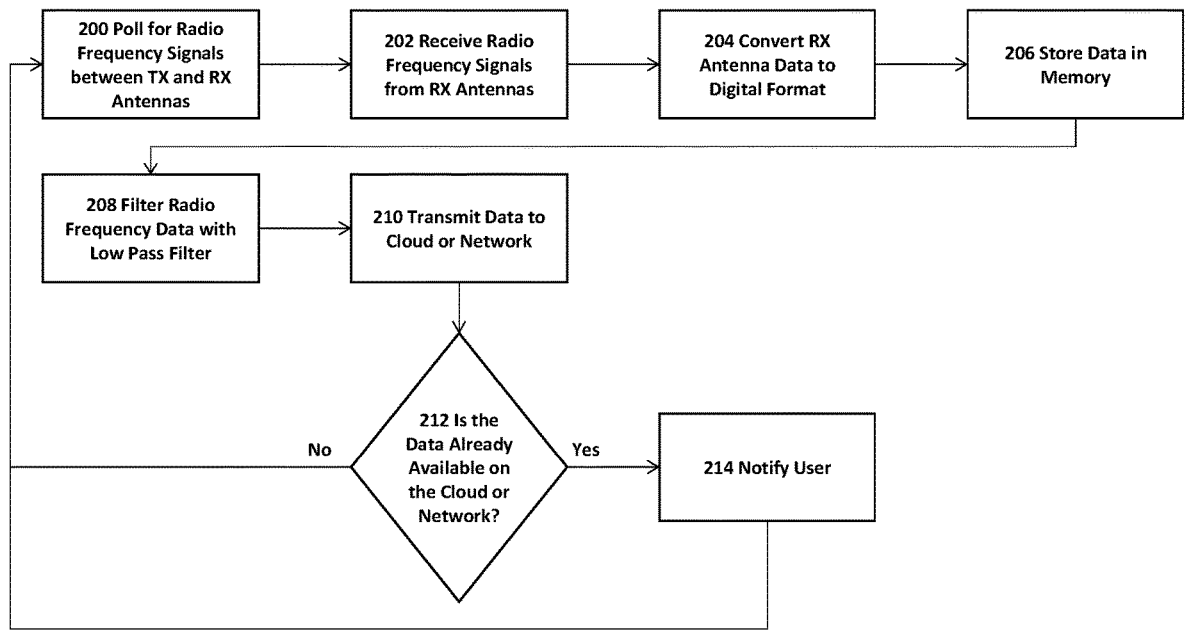
FIG. 2: Illustrates an example operation of a Device Base Module, according to an embodiment.

FIG. 2 illustrates an example operation of the device base module 124. The process may begin with the device base module 124 polling the Active Range RF signals between the one or more TX antennas 110 and the one or more RX antennas 164 at step 200. The device base module 124 may be configured to read and process instructions stored in the memory 114 using the processor 118. The TX antennas 110 may be configured to transmit RF signals in the RF Activated Range from 500 MHZ to 300 GHZ. For example, the one or more TX antennas 110 may use RF signals at a range of 500 MHZ to 300 GHZ. The device base module 124 may receive the RF frequency signals from the one or more RX antennas 164 at step 202. For example, an RX antenna receives an RF frequency range of 300-330 GHz from the patient's blood. The device base module 124 may be configured to convert the received RF signals into a digital format using the ADC 112 at step 204. For example, the received RF signals of frequency range 300-330 GHz is converted into a 10-bit data signal. The device base module 124 may be configured to store converted digital format into the memory 114 at step 206. The device base module 124 may be configured to filter the stored RF signals at step 208. The device base module 124 may be configured to filter each RF signal using a low pass filter. For example, the device base module 124 filters the RF signals of frequency range 300-330 GHz to the RF of frequency range 300-310 GHz The device base module 124 may be configured to transmit the filtered RF signals to the cloud or other network using the comms 120 at step 210. For example, the device base module 124 may be configured to transmit RF signals in the RF Activated Range from 500 MHZ to 300 GHZ to the cloud. The device base module 124 may be configured to determine whether the transmitted data is already available in the cloud or other network at step 212. The device base module 124, using the comms 120, communicates with the cloud network to determine that the transmitted RF signal is already available. The device base module 124 may determine that the transmitted data is not already present in the cloud. The device base module 124 may be redirected back to step 200 to poll the RF signals between the one or more TX antennas 110 and the one or more RX antennas 164. For example, the device base module 124 determines that the transmitted RF in the RF Activated Range from 500 MHZ to 300 GHZ is not present in the cloud, and corresponding to the transmitted signal, there is no data related to the blood glucose level of the patient. The device base module 124 may determine that transmitted data is already in the cloud. For example, the device base module 124 reads cloud notification of the patient's blood glucose level as 110 mg/dL corresponding to an RF in the RF Activated Range from 500 MHZ to 300 GHZ. The device base module 124 may continue to step 214. The device base module 124 may notify the user via the device 108 of health information, for example, blood glucose level.

Figure 3:
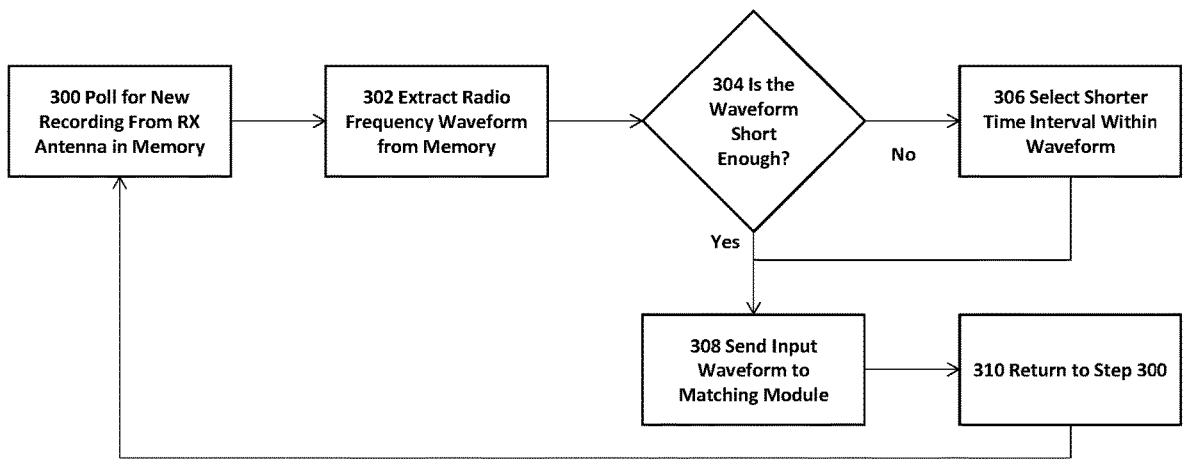
FIG. 3: Illustrates an example operation of an Input Waveform Module, according to an embodiment.

FIG. 3 illustrates an example operation of the input waveform module 126. The process may begin with the input waveform module 126 polling, at step 300, for newly recorded data from the RX antennas 164 stored in memory 114. The input waveform module 126 may extract, at step 302, the recorded radio frequency waveform from memory. If there is more than one waveform recorded, the input waveform module 126 may select each waveform separately and loop through the following steps. The input waveform module 126 may determine, at step 304, if the waveform is small enough to be an input waveform for the matching module 128. This will depend on the computational requirements and/or restrictions of the matching module 128. If the waveform is short enough, the input waveform module 126 may skip to step 308. If the waveform is too long, the input waveform module 126 may select, at step 306, a shorter time interval within the entire recorded waveform. For example, if the waveform is 5 minutes long, then only a 30-second interval may be selected. The interval may be selected at random or by a selection process. The input waveform module 126 may send, at step 308, the input waveform to the matching module 128. The input waveform module 126 may then return, at step 310, to step 300.

Figure 4:
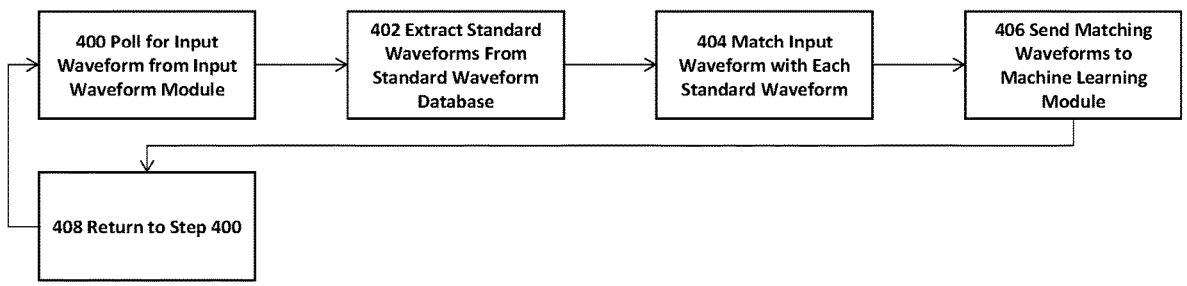
FIG. 4: Illustrates an example operation of a Matching Module, according to an embodiment.

FIG. 4 illustrates an example operation of the matching module 128. The process may begin with the matching module 128 polling, at step 400, for an input waveform from the input waveform module 126. The matching module 128 may extract, at step 402, each standard waveform from the standard waveform database 116. The matching module 128 may match, at step 404, the input waveform with each standard waveform. Matching may be determining which standard waveforms the input waveform is similar to. Matching may involve convolution and/or cross-correlation of the waveforms or any other suitable matching technique. Cross-correlation and convolution are mathematical operations that can be used to determine the similarity between two wave functions. They are often used in signal processing and image recognition applications to find patterns or features in data. Cross-correlation is a measure of the similarity between two signals as a function of the time lag applied to one of them. It is defined as the integral of the product of two signals after one is flipped and delayed by some amount. By running the cross-correlation function on two wave functions, the output will give a similarity value between two signals, where the highest value represents the most similar pair. Convolution, on the other hand, is a mathematical operation that combines two functions to produce a third function. It is the integral of the product of two functions after one of them is flipped and then shifted. By applying convolution on two wave functions, the output will be a function in which values represent the degree of similarity between input signals, where higher values represent more similar signals. These operations may be used in combination and/or with other techniques, such as Fourier transform, to extract information from signals and compare them. Matching waveforms may be waveforms where the cross-correlation and/or convolution values are close to 1 with respect to time. For example, the threshold value may be 0.85. Any point in the function that results from cross-correlation that is above 0.85 may indicate that the standard waveform matches the input waveform. Matching standard waveforms, the input waveform, the cross-correlation of both, and/or the convolution of both may be used as an input to the machine learning algorithm of the machine learning module 130. The matching module 128 may send, at step 406, the matching waveforms to the machine learning module 130. Matching waveforms may refer to the standard waveforms that were similar to the input waveform, the waveforms that were generated via convolution and/or cross-correlation, or both. The matching module 128 may then return, at step 408, to step 400.

Figure 5:
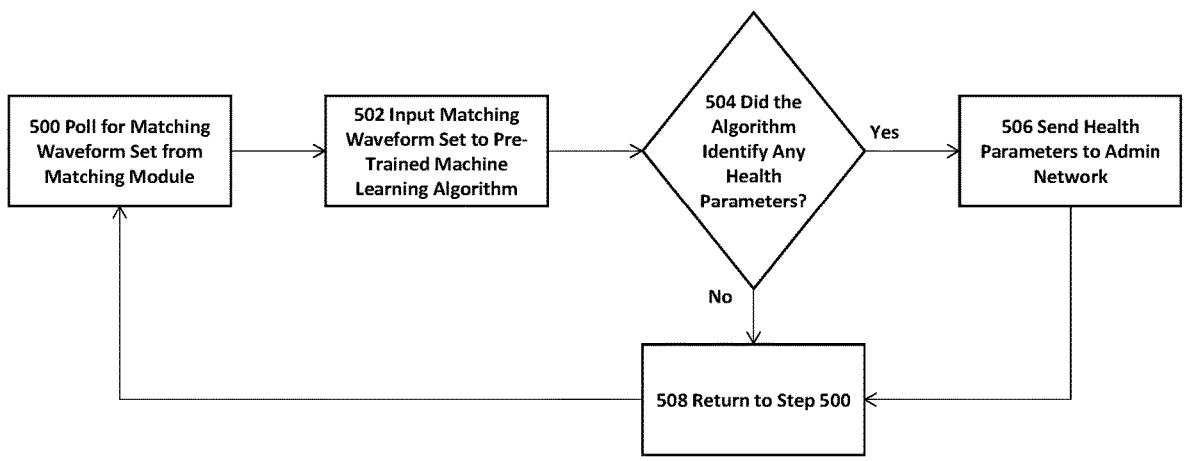
FIG. 5: Illustrates an example operation of a Machine Learning Module, according to an embodiment.

FIG. 5 illustrates an example operation of the machine learning module 130. The process may begin with the machine learning module 130 polling, at step 500, for a set of matching waveforms from the matching module 128. Matching waveforms may be a set of standard waveforms that are similar to the input waveform or statistical combinations of the input waveform and standard waveforms, such as convolutions or cross-correlations. The machine learning module 130 may input, at step 502, the set of received waveforms into a pre-trained machine learning algorithm. The machine learning algorithm may be trained on similar sets of matched waveforms where the input waveform is from a patient whose health parameters are known. The waveforms may be input directly into the algorithm, such as a set of X and Y values. The matching waveforms may each be summarized as a closest fit function or may be transformed into a set of sine waves using a Fourier transform. Training data should be labeled with the correct output, such as the type of waveform. In order to prepare the data, the waveforms need to be processed and converted into a format that can be used by the algorithm. Once the data is prepared, the algorithm is trained on the labeled data. The model uses this data to learn the relationships between the waveforms and their corresponding outputs. During the training process, the model will adjust its parameters to minimize the error between its predictions and the correct outputs. Once the model has been trained and fine-tuned, it can be used to recognize waveforms in new, unseen data. This could be done by giving the input waveforms, then the algorithm will predict the health parameters. The machine learning module 130 may determine, at step 504, if the algorithm identified any health parameters. Identification may require a certain interval of confidence. For example, if the machine learning algorithm determines that it is more than 70% likely that a health parameter is correct, then that parameter may be considered identified. If multiple conflicting parameters exist, then the most confident may be used. For example, if the algorithm determines that it is 75% likely that the patient's blood glucose level is between 110-115 mg/dL and 90% likely that the patient's blood glucose is between 105-110 mg/dL, then the more confident value of 105-110 mg/dL may be identified. If none of the results from the machine learning algorithm are above the confidence threshold, or the results are otherwise inconclusive, the machine learning module 130 may skip to step 508. If any health parameters were identified, the machine learning module 130 may send, at step 506, the health parameters to the notification module 136. The machine learning module 130 may then return, at step 508, to step 500.

Figure 6:
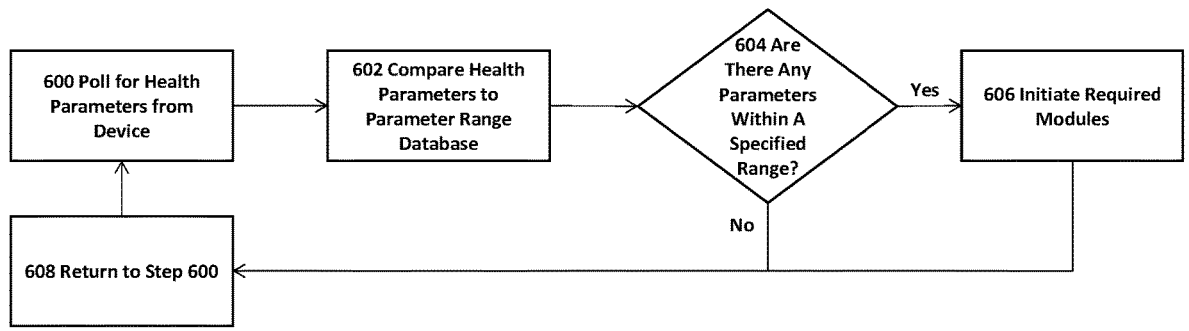
FIG. 6: Illustrates an example operation of a Base Module, according to an embodiment.

FIG. 6 illustrates an example operation of the base module 134. The process may begin with the base module 134 polling, at step 600, for health parameters from the device 108. The base module 134 may compare, at step 602, health parameters to the health parameter range in the parameter range database 148. The base module 134 may determine, at step 604, if any of the received parameters fall within a range in the parameter range database 148. If not, the base module may skip to step 608. If any of the received parameters fall within a range in the parameter range database 148, the base module 134 may initiate, at step 606, the modules required to perform the actions associated with that range. For example, blood glucose levels in the range of 120 mg/dL to 180 mg/dL may be associated with a notification of the patient and/or doctor, which would require the notification module 136. For another example, blood glucose levels in the range of 120 mg/dl to 180 mg/dL may be associated activation of an insulin pump which would require the device module 138. For another example, blood glucose levels in the range of 120 mg/dL to 180 mg/dL may be associated with a need to run a pre-diabetes screening which would require the guidance module 140. For another example, blood glucose levels in the range of 120 mg/dL to 180 mg/dL may be associated with a need for a more comprehensive reporting of the patient's glucose levels which would require the report schedule module 142. For another example, blood glucose levels in the range of 120 mg/dL to 180 mg/dL may be associated with a questionnaire involving diet and eating habits which would require the virtual assistant module 144. For another example, blood glucose levels in the range of 120 mg/dL to 180 mg/dL may be associated with a need to remind the patient to take medication which would require the medication module 146. The base module 134 may send the relevant parameters to the initiated modules and/or the associated actions. The base module 134 may then return, at step 608, to step 600.

Figure 7:
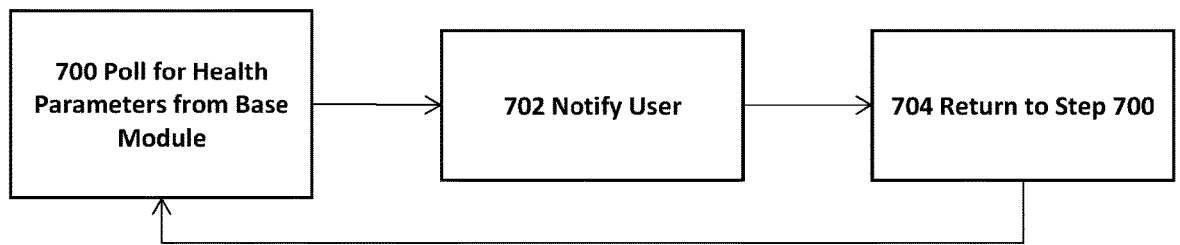
FIG. 7: Illustrates an example operation of a Notification Module, according to an embodiment.

FIG. 7 illustrates an example operation of the notification module 136. The process may begin with the notification module 136 being initiated, at step 700, by the base module 134. The notification module 136 may receive a notification action or actions from the base module 134 or may receive the relevant health parameters, which can then be compared to the parameter range database 148 to determine the associated actions. The notification module 136 may notify, at step 702, the user of the device and/or their care providers. For example, the device may display a readable interface with the identified health parameters such as heart rate, blood pressure, blood glucose, oxygen level, etc. This information may be sent to another device, such as a terminal in a nursing station, doctor's office, emergency medical transport office, etc. Notification may include audio or haptic feedback such as beeping or vibrating. The notification module 136 may then return, at step 704, to step 700.

Figure 8:
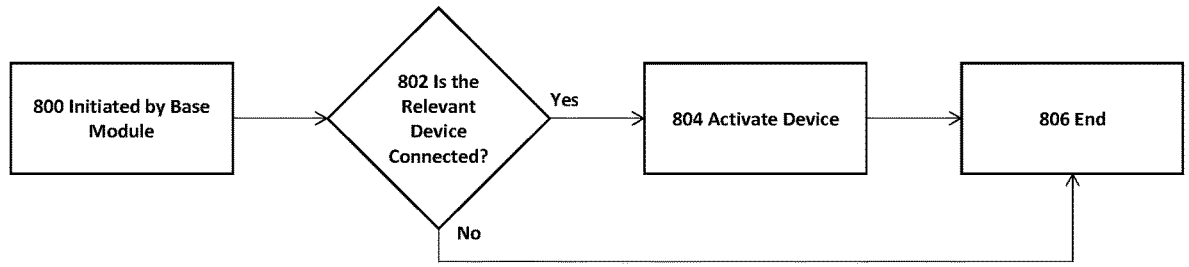
FIG. 8: Illustrates an example operation of a Device Module, according to an embodiment.

FIG. 8 illustrates an example operation of the device module 138. The process may begin with the device module 138 being initiated, at step 800, by the base module 134. The device module 138 may receive a device action or actions from the base module 134 or may receive the relevant health parameters, which can then be compared to the parameter range database 148 to determine the associated actions. Device actions may be activating or initiating a device, but may also be other actions, such as changing the settings of a device or turning off a device. The device module 138 may determine, at step 802, if the relevant device or devices are connected to the admin network 132. If a device is not connected, the device module 138 may end and/or notify a user or admin that the device is not connected. If the relevant device or devices are connected, the device module 138 may activate, at step 804, the relevant device. For example, the triggering health parameter may be 1 ppm of COVID-19 in the patient's blood which may cause the system to activate via the device module 138, a blood oxygen measurement device, due to a concern of hypoxia. The device module 138 may then end at step 806.

Figure 9:
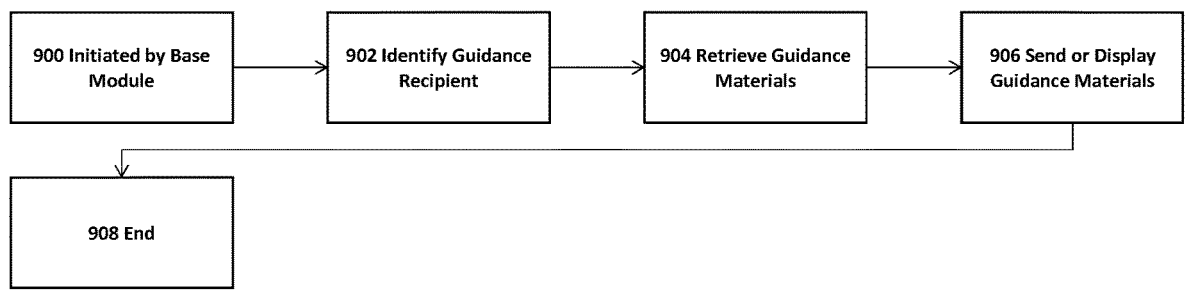
FIG. 9: Illustrates an example operation of a Guidance Module, according to an embodiment.

FIG. 9 illustrates an example operation of the guidance module 140. The process may begin with the guidance module 140 being initiated, at step 900, by the base module 134. The guidance module 140 may receive a guidance action or actions from the base module 134 or may receive the relevant health parameters, which can then be compared to the parameter range database 148 to determine the associated actions. Guidance actions may be sending or displaying advice or information to the patient, health professionals, family of the patient, or any other person who may benefit from the advice or information. The guidance module 140 may identify, at step 902, the person who may receive guidance, such as the patient, health professionals, family of the patient, etc. There may be more than one recipient of guidance information. The guidance module 140 may retrieve, at step 904, guidance materials. These materials may be available in a database on the admin network 132 or somewhere they can be retrieved through the cloud 150, such as a website or server. The guidance materials may be generated by a module which may use AI language modules. Guidance materials may include advice or information for patients, such as activities or habits that would alleviate issues in the triggering health parameter. For example, if the triggering health parameter is cortisol, the guidance materials may include meditation exercises. Guidance materials may include actions to be taken by the patient's doctor or other health professionals. For example, if the triggering health parameter is glucose level, the guidance materials may advise a doctor to screen for diabetes or pre-diabetes. The guidance module 140 may send, at step 906, the guidance materials to the intended recipient. If the recipient is connected to the admin network 132, then the materials may be displayed to them via a terminal or device such as a computer or smartphone. If the recipient is not on the admin network 132, then the guidance materials may be sent to an email, text to a phone number, faxed, or otherwise delivered to the recipient. The guidance module 140 may then end at step 908

Figure 10:
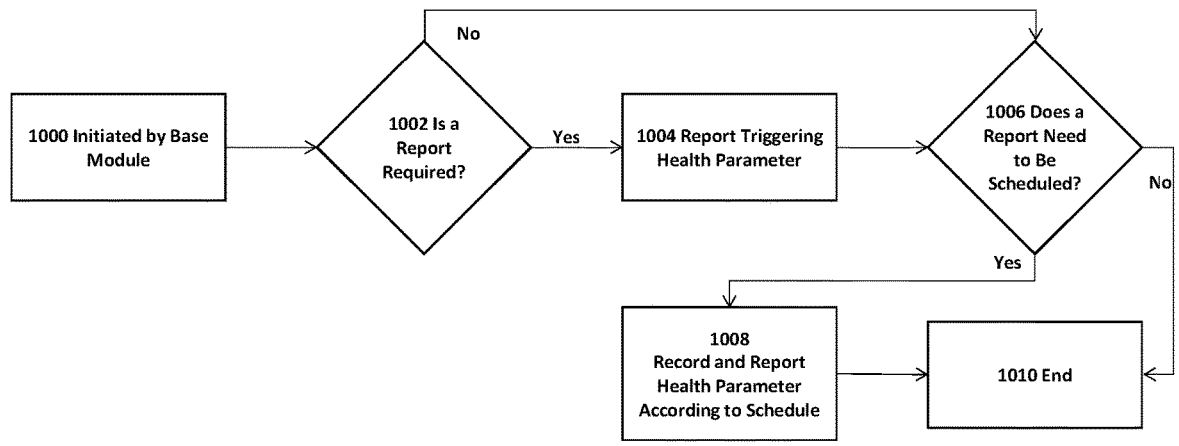
FIG. 10: Illustrates an example operation of a Report Schedule Module, according to an embodiment.

FIG. 10 illustrates an example operation of the report schedule module 142. The process may begin with the report schedule module 142 being initiated, at step 1000, by the base module 134. The report schedule module 142 may receive a report action or actions from the base module 134 or may receive the relevant health parameters, which can then be compared to the parameter range database 148 to determine the associated actions. Reports actions may be reporting a health parameter or setting up a report schedule for a health parameter which may include more than just the event that triggered a report. The report schedule module 142 may determine, at step 1002, if a report is required at this time. For example, if the triggering health parameter is elevated glucose levels, each triggering circumstance may be reported. A report may only be warranted when the blood glucose levels enter the triggering range, but no additional reports may be required until blood glucose levels fall back into normal ranges. If no report is required at this time, the report schedule module 142 may skip to step 1006. If a report is required, the report schedule module 142 may report, at step 1004, the triggering health parameter. The report may include the health parameter measurements when and/or around the time the report was triggered. The report may include other relevant information, such as other health parameters of the patient, the activity the patient was involved in, the location of the patient, etc. A report may be saved in a database and/or sent to relevant parties, such as the patient and their care providers. The report schedule module 142 may determine, at step 1006, if a report needs to be scheduled. Health parameters within a triggering range may be cause for more data to be collected over time and sent as a more comprehensive report. If there is already a scheduled report for this health parameter, it may be overwritten or amended, or the report schedule module may end. The report schedule module may end if no report needs to be scheduled. If a report needs to be scheduled, the report schedule module 142 may record and report, at step 1008, the relevant health parameter at times according to the schedule. For example, the triggering health parameter may be blood glucose at a high level. But, high blood glucose can be caused by eating a meal and is unrelated to diabetes. When high blood glucose falls into a triggering range, a report schedule may begin that records blood glucose levels over the course of a week and then send a comprehensive report to a health professional at the end of the week. The report schedule module 142 may then end at step 1010. The report schedule module 142 may not end until all pending reports are sent.

Figure 11:
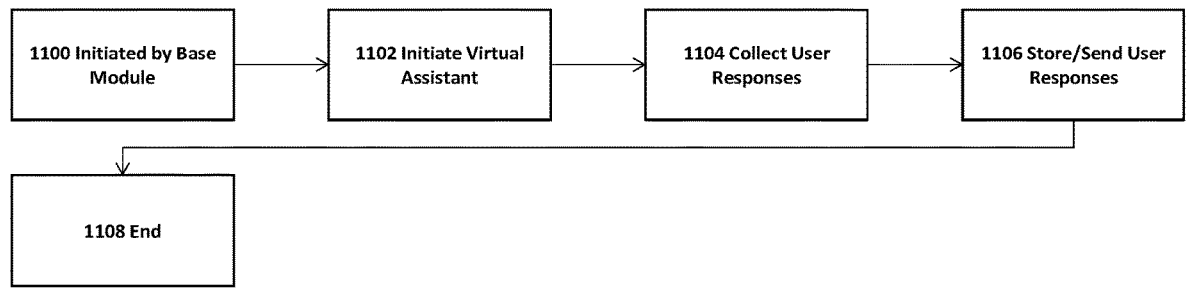
FIG. 11: Illustrates an example operation of an Assistant Module, according to an embodiment.

FIG. 11 illustrates an example operation of the assistant module 144. The process may begin with the assistant module 144 being initiated, at step 1100, by the base module 134. The assistant module 144 may receive an assistant action or actions from the base module 134 or may receive the relevant health parameters, which can then be compared to the parameter range database 148 to determine the associated actions. Assistant actions may be questions or advice a virtual assistant may have for the patient or health professionals. The assistant module 144 may initiate virtual assistant software at step 1102, which may be run on the admin network 132 or through a third-party virtual assistant service. The virtual assistant is a bot that may send and receive text and other information. The virtual assistant may ask a user questions that may be stored in a database or generated using natural language AI. The virtual assistant may provide information or advice for patients, such as activities or habits that would alleviate issues in the triggering health parameter. For example, the virtual assistant may suggest meditation exercises if the triggering health parameter is cortisol. The assistant module 144 may collect, at step 1104, user responses to questions asked by the virtual assistant. The virtual assistant may also collect all responses from the user even if a question was not asked. The assistant module 144 may store and/or send, at step 1106, the collected user responses. The responses may be stored in a database on the admin network 132 or on the cloud 150. The responses may be sent to a health professional such as the patient's doctor, another module in the system, a third-party data center, or any other party which may use the responses. The assistant module 144 may then end at step 1108. The assistant module 144 may not end until a user closes the virtual assistant software.

FIG. 12 illustrates an example operation of the medication module 146. The process may begin with the medication module 146 being initiated, at step 1200, by the base module 134. The medication module 146 may receive an action or actions from the base module 134 or the relevant health parameters, which can then be compared to the parameter range database 148 to determine the associated actions. Medication actions may be reminders or warnings for a patient or health professional to take, stop, or adjust the medication dosage. The medication module 146 may check, at step 1202, the medication schedule for the medicine called for by the medicine action. For example, if the triggering parameter is blood glucose level, then the medicine called for by the medicine action may be insulin. The medication schedule may be the normal schedule at which a medicine is administered or the minimum window for which the medicine can be administered. For example, some medications may be harmful to take more than two doses in 4 hours. The medication schedule may be stored on a database on the admin network 132 or available on or through the cloud 150. A doctor or other health professional may customize a medication schedule for a patient. The medication module 146 may determine, at step 1204, if the medication should be taken at this time. For example, if the triggering health parameter is glucose level, and the glucose level range is dangerously high, then insulin should be taken. The medication module 146 will take into account the medication schedule so that medication does not overdose. The medication schedule may be ignored if health parameters are in critical ranges or if it can be determined that taking the medication immediately would be less harmful than waiting until the medication schedule allows. If the medication should be taken, the medication module 146 may inform, at step 1206, the user that the medication can and/or should be taken or administered at this time. The medication module 146 may then end. If the medication should not be taken, the medication module 146 may determine, at step 1208, if the medication should be stopped or adjusted. For example, the triggering health parameter may be blood urea nitrogen, indicating kidney function. If the medication has a known side effect on kidney function, then the medication may need to be stopped or adjusted so that the patient does not suffer kidney damage. If the medication should be stopped or adjusted, the medication module 146 may inform, at step 1210, the user to adjust or stop the medication regimen or, if the user is the patient, speak with their care provider about stopping or adjusting the medication regimen. The medication module 146 may then end at step 1212

FIG. 13 displays the parameter range database 148. The parameter range database 148 may contain ranges of health parameter values and an action or actions which are associated with that range. When health parameters are within range, the associated actions may be carried out by the modules of the system.

Figure 14:
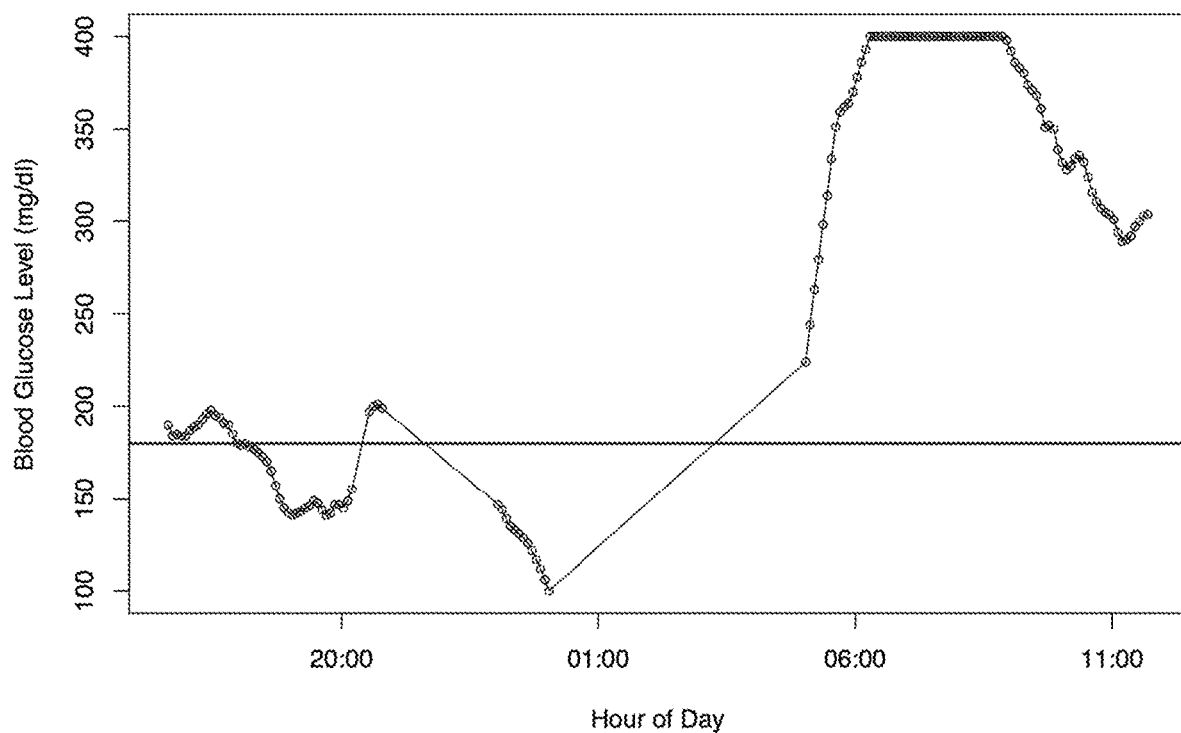
FIG. 14: Illustrates an example of a Glucose Waveform, according to an embodiment.

FIG. 14 displays an example of a glucose waveform. The figure shows blood glucose levels in a patient recorded over time. A computer can store a waveform by digitizing the analog signal and storing the resulting digital values in memory. Digitization is typically accomplished by an analog-to-digital converter (ADC), which samples the amplitude of the analog signal at regular intervals and converts each sample to a digital value. The resulting digital values and information about the sampling rate and bit depth can be used to reconstruct the original waveform when the data is played back. The digital values could be stored in an array or binary files. The computer may store the important parts of the waveform, such as local and/or absolute maxima and minima, inflection points, inversion points, average value, best fit line or function, etc.

Figure 15:
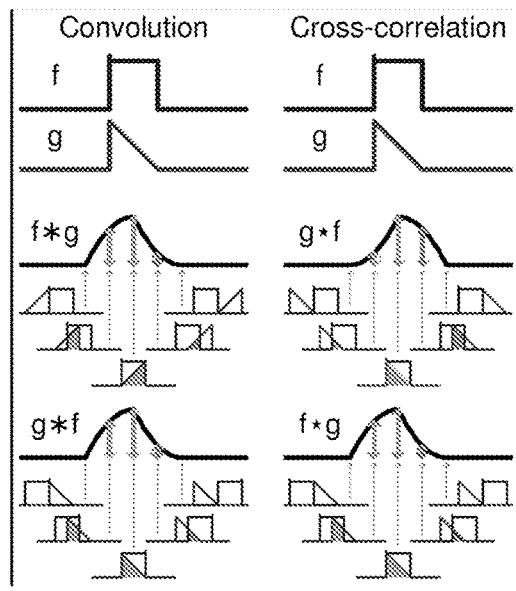
FIG. 15: Illustrates an example of Matching Methods, according to an embodiment.

FIG. 15 displays an example of matching methods such as convolution and cross-correlation. The figure illustrates two different matching methods, convolution, and cross-correlation. In the convolution process, the standard waveform slides over the input waveform, element-wise multiplying and summing the overlapping values. The result is a new output waveform. The convolution operation is useful for detecting specific features, such as edges, in the input waveform. In the cross-correlation process, the standard waveform is also sliding over the input waveform, element-wise multiplying and summing the overlapping values. However, the output waveform is not generated by summing the product of the standard waveform and the overlapping part of the input waveform but by taking the dot product of the standard waveform and the input waveform. The cross-correlation operation is used to find patterns in the input waveform that are similar to the standard waveform. Convolution and cross-correlation are similar operations used for waveform processing and pattern recognition. They are widely used in image processing, machine learning, computer vision, and waveform processing applications. This is a general description; these methods' actual implementation will depend on the specific use case and application.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The invention claimed is:

1. A method of recommending medical guidance based on data resulting from at least two noninvasive radio-frequency (RF) analyte measurements on a patient, comprising;
  (a) providing a non-invasive RF analyte measurement device that is configured to conduct the at least two noninvasive RF analyte measurements on the patient to measure at least two different real-time analytes in the patient, the non-invasive RF analyte measurement device comprises at least one transmit antenna that transmits RF transmit signals into the patient and at least one receive antenna that detects RF signals using at least one receive antenna that result from transmitting the RF transmit signals into the patient;
  (b) providing an electronic database that is in electronic communication with the non-invasive RF analyte measurement device, the electronic database containing a plurality of health parameter value ranges for two or more different stored analytes, each one of the plurality of health parameter value ranges having a combination of at least two corresponding actions and at least two corresponding executable modules selected from a group consisting of a device module, a guidance module, a report schedule module, an assistant module, and a medication module, each one of the plurality of health parameter value ranges and its combination of the at least two corresponding actions and the at least two corresponding executable modules are different from each other health parameter value range, and its combination of the at least two corresponding actions, and the at least two corresponding executable modules, the at least two corresponding actions in the electronic database being executable by two or more of the device module that is connected to one or more additional devices that can be actuated by the device module, the guidance module that is configured to electronically send guidance to a recipient, the report schedule module that is configured to electronically send a report on the patient's health parameters to the patient or a patient care provider, the assistant module that is configured to activate a virtual assistant that electronically collects information from the patient and/or electronically provides medical advice to the patient, and the medication module that is configured to electronically send medication notices to the patient or patient care provider;
  (c) triggering noninvasive RF analyte measurements using the non-invasive RF analyte measurement device by transmitting the RF transmit signals into the patient using the at least one transmit antenna and detecting the RF signals using the at least one receive antenna that result from transmitting the RF transmit signals into the patient, and converting the detected RF signals from analog to digital signals using an analog to digital converter;
  (d) using a processor to calculate at least two analyte ranges of the at least two different real-time analytes over time based on the digital signals;
  (e) comparing the at least two calculated analyte ranges to one or more of the plurality of health parameter value ranges in the electronic database, and based on the comparing, selecting one of the at least two corresponding actions; and
  (f) executing the selected one of the at least two corresponding actions using the device module, the guidance module, the report schedule module, the assistant module, or the medication module.

2. The method of claim 1, wherein (c), (d), (e) and (f) are performed in real-time.

3. The method of claim 1, wherein the real-time analyte comprises glucose and one of the stored analytes comprises glucose.

4. The method of claim 1, wherein the one or more additional devices comprise a second non-invasive RF analyte measurement device, a blood pressure monitor, a blood oxygen monitor, an infusion pump, or a ventilator.

5. The method of claim 1, further comprising:
  determining motion levels of the patient during the non-invasive RF analyte measurements using at least one motion sensor, and comparing the motion levels to a motion threshold; and
  if the motion levels exceed the motion threshold, indicating the calculated analyte range as potentially inaccurate.

6. A medical guidance system that guides medical care of a patient based on data resulting from at least two noninvasive radio-frequency (RF) analyte measurements on the patient, comprising:
  a non-invasive RF analyte measurement device that is configured to conduct the at least two noninvasive RF analyte measurements on the patient to measure at least two real-time analytes in the patient, the non-invasive RF analyte measurement device comprises at least one transmit antenna that transmits RF transmit signals into the patient and at least one receive antenna that detects RF signals using at least one receive antenna that result from transmitting the RF transmit signals into the patient;
  an analog to digital converter in electronic communication with the at least one receive antenna that converts the RF signals detected by the at least one receive antenna from analog to digital;
  an electronic database in electronic communication with the non-invasive RF analyte measurement device, the electronic database containing a plurality of health parameter value ranges of two or more different stored analytes, each one of the plurality of health parameter value ranges having a combination of at least two corresponding actions and at least two corresponding executable modules selected from a group consisting of a device module, a guidance module, a report schedule module, an assistant module, and a medication module, each one of the plurality of health parameter value ranges and its combination of at least two corresponding actions, and at least two corresponding executable modules are different from each other health parameter value range and its combination of at least two corresponding actions and at least two corresponding executable modules; and at least two of the following in electronic communication with the non-invasive RF analyte measurement device: the device module connected to one or more additional devices that can be actuated by the device module; the guidance module that is configured to electronically send guidance to a recipient; the report schedule module that is configured to electronically send a report on the patient's health parameters to the patient or a patient care provider; the assistant module that is configured to activate a virtual assistant that electronically collects information from the patient and/or electronically provides medical advice to the patient; the medication module that is configured to electronically send medication notices to the patient or patient care provider.

7. The medical guidance system of claim 6, wherein the real-time analyte comprises glucose and one of the stored analytes comprises glucose.

8. The medical guidance system of claim 6, wherein the one or more additional devices comprise a second non-invasive RF analyte measurement device, a blood pressure monitor, a blood oxygen monitor, an infusion pump, or a ventilator.

9. The medical guidance system of claim 6, further comprising at least one motion sensor that senses motion of the patient during the noninvasive RF analyte measurements.

* * * * *